(12) United States Patent
Kim et al.

(10) Patent No.: US 11,975,308 B2
(45) Date of Patent: *May 7, 2024

(54) DEHYDRATION CATALYST, METHOD FOR PREPARING THE SAME, AND METHOD OF PREPARING ALKENE USING THE SAME

(71) Applicant: LG CHEM, LTD., Seoul (KR)

(72) Inventors: Hyeon Bin Kim, Daejeon (KR); Joo Young Cheon, Daejeon (KR); Young Sub Keum, Daejeon (KR); Dae Heung Choi, Daejeon (KR)

(73) Assignee: LG Chem, Ltd., Seoul (KR)

( * ) Notice: Subject to any disclaimer, the term of this patent is extended or adjusted under 35 U.S.C. 154(b) by 372 days.

This patent is subject to a terminal disclaimer.

(21) Appl. No.: 17/424,815

(22) PCT Filed: Nov. 16, 2020

(86) PCT No.: PCT/KR2020/016108
§ 371 (c)(1),
(2) Date: Jul. 21, 2021

(87) PCT Pub. No.: WO2021/256627
PCT Pub. Date: Dec. 23, 2021

(65) Prior Publication Data
US 2022/0258132 A1   Aug. 18, 2022

(30) Foreign Application Priority Data

Jun. 19, 2020 (KR) .......................... 10-2020-0074932
Nov. 6, 2020 (KR) .......................... 10-2020-0147797

(51) Int. Cl.
| | | |
|---|---|---|
| B01J 21/04 | (2006.01) | |
| B01J 21/00 | (2006.01) | |
| B01J 35/61 | (2024.01) | |
| B01J 35/63 | (2024.01) | |
| B01J 37/08 | (2006.01) | |
| B01J 37/10 | (2006.01) | |
| C07C 1/24 | (2006.01) | |

(52) U.S. Cl.
CPC .............. *B01J 21/04* (2013.01); *B01J 35/613* (2024.01); *B01J 35/633* (2024.01); *B01J 35/635* (2024.01); *B01J 37/082* (2013.01); *B01J 37/10* (2013.01); *C07C 1/24* (2013.01); *C07C 2521/04* (2013.01)

(58) Field of Classification Search
None
See application file for complete search history.

(56) References Cited

U.S. PATENT DOCUMENTS

| | | | |
|---|---|---|---|
| 5,227,563 A | 7/1993 | Fukuhara et al. | |
| 5,475,183 A | 12/1995 | Araki et al. | |
| 10,010,877 B2 | 7/2018 | Jothimurugesan et al. | |
| 2005/0033101 A1 | 2/2005 | Voskoboynikov et al. | |
| 2006/0099421 A1 | 5/2006 | Yen et al. | |
| 2008/0085225 A1* | 4/2008 | Bhan ...................... | C10G 49/04 422/600 |
| 2018/0369788 A1* | 12/2018 | Liu ......................... | B01J 21/04 |
| 2020/0010393 A1* | 1/2020 | Vautravers ........... | B01J 37/0236 |
| 2022/0314197 A1* | 10/2022 | Keum ..................... | B01J 37/10 |
| 2022/0341356 A1* | 10/2022 | Takeda ................. | B01J 37/0215 |

FOREIGN PATENT DOCUMENTS

| | | |
|---|---|---|
| CN | 1079417 A | 12/1993 |
| CN | 1604815 A | 4/2005 |
| CN | 1649672 A | 8/2005 |
| CN | 102416325 A | 4/2012 |
| CN | 106458786 A | 2/2017 |
| CN | 110354837 A | 10/2019 |
| EP | 3092211 B1 | 6/2017 |
| JP | S55116623 A | 9/1980 |
| JP | H03127745 A | 5/1991 |
| JP | 2003531712 A | 10/2003 |
| JP | 2014181201 A | 9/2014 |
| KR | 10-1997-0009880 A | 3/1997 |
| KR | 10-2004-0065270 A | 7/2004 |
| KR | 10-2018-0081659 A | 7/2018 |
| WO | 2015/084041 A1 | 6/2015 |
| WO | 2015170686 A1 | 11/2015 |
| WO | 2019229061 A1 | 12/2019 |

OTHER PUBLICATIONS

Janlamool, et al.(2017). Catalytic Ethanol Dehydration to Ethylene over Nanocrystalline χ- and γ-Al2O3 Catalysts, Journal of Oleo Science, vol. 66(9), pp. 1029-1039.

* cited by examiner

*Primary Examiner* — Tam M Nguyen
(74) *Attorney, Agent, or Firm* — Bryan Cave Leighton Paisner LLP

(57) ABSTRACT

The present disclosure relates to a dehydration catalyst, a method for preparing the same, and a method for preparing an alkene using the same. More particularly, the present invention relates to a dehydration catalyst that is mixed-phase alumina including 1 to 18% by weight of alpha-alumina, 65 to 95% by weight of theta-alumina, and 4 to 34% by weight of delta-alumina, a method for preparing the dehydration catalyst, and a method for preparing an alkene using the dehydration catalyst.

15 Claims, 2 Drawing Sheets

[FIG. 1]
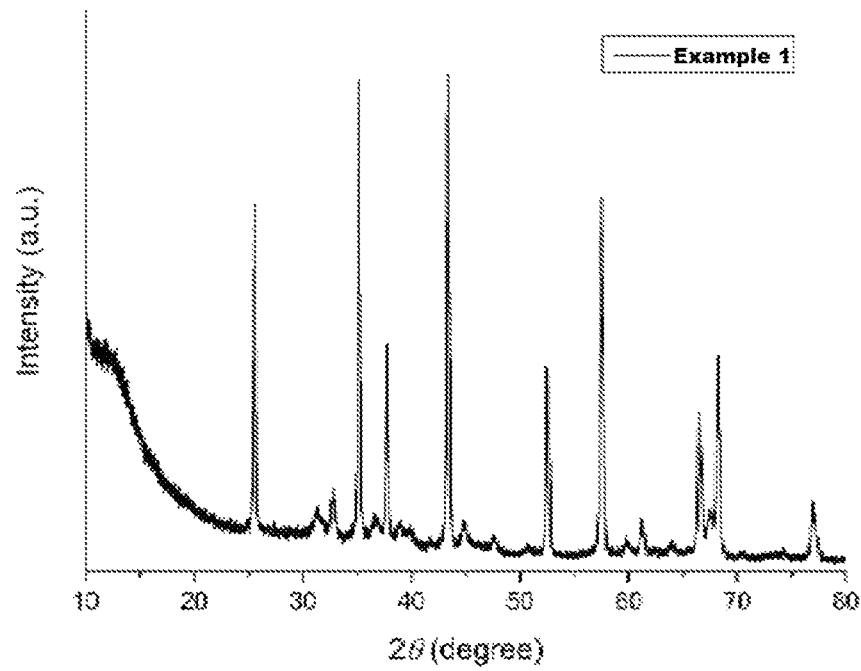
[FIG. 2]
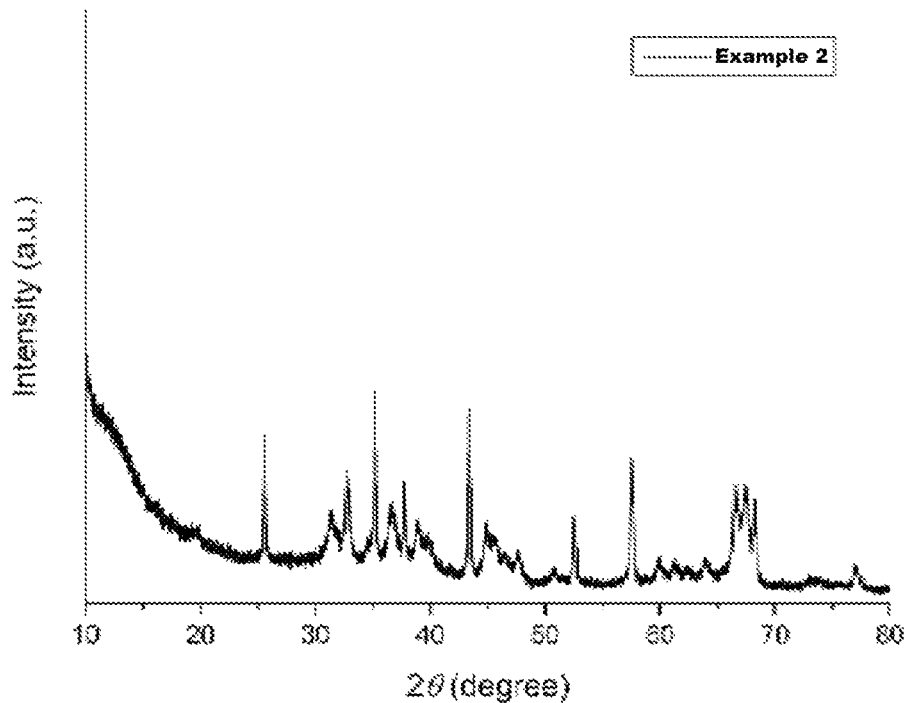

[FIG. 3]
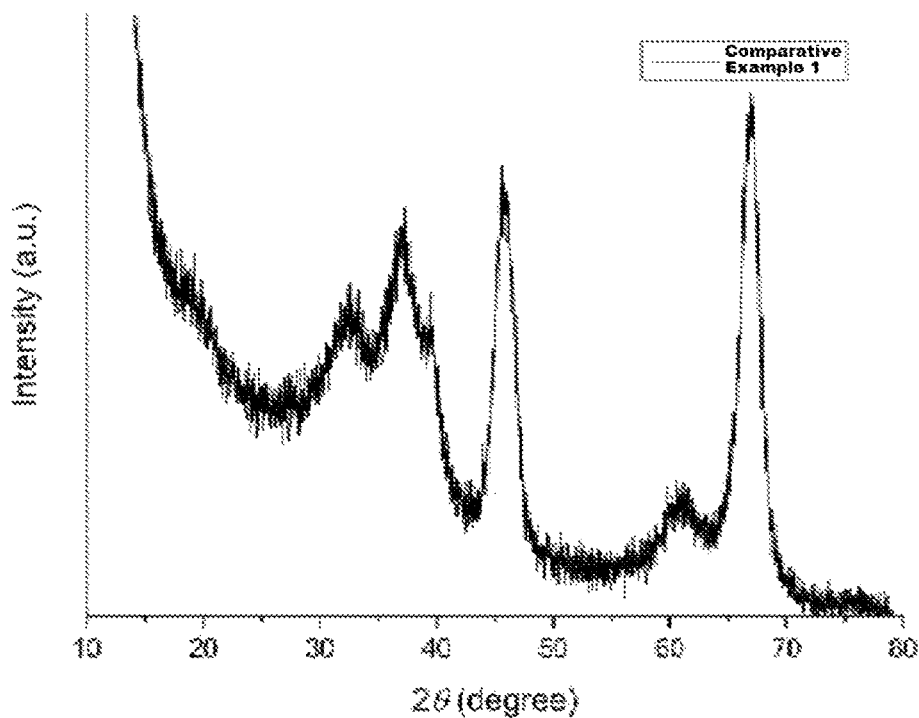
[FIG. 4]
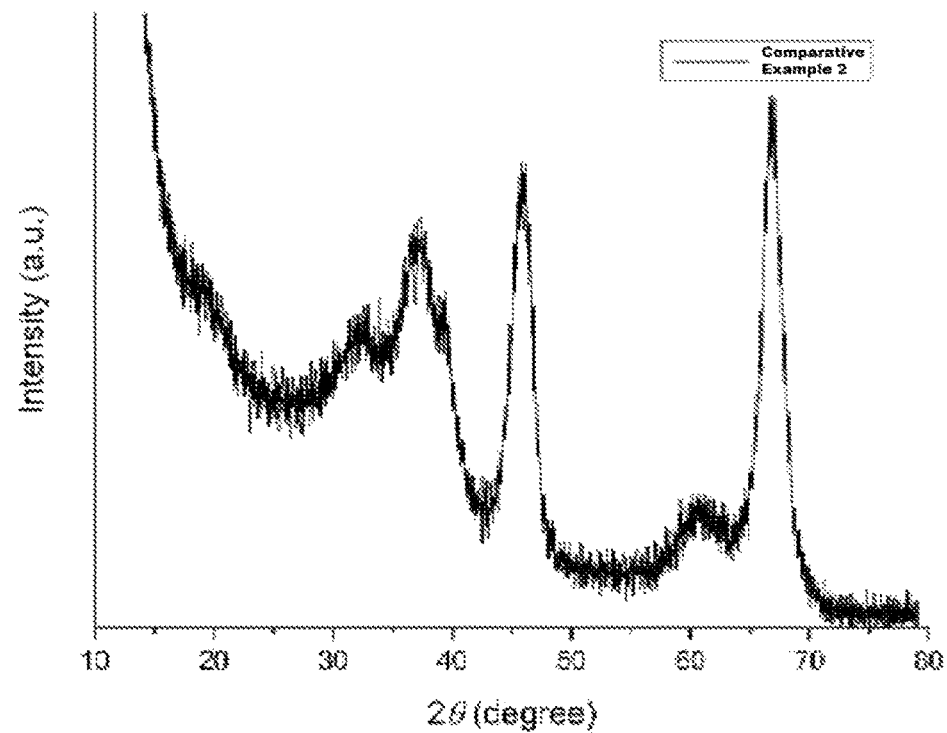

DEHYDRATION CATALYST, METHOD FOR PREPARING THE SAME, AND METHOD OF PREPARING ALKENE USING THE SAME

CROSS-REFERENCE TO RELATED APPLICATIONS

This application is a National Phase entry pursuant to U.S.C. § 371 of International Application No. PCT/KR2020/016108, filed on Nov. 16, 2020, and claims priority to and the benefit of Korean Patent Application No. 10-2020-0074932, filed on Jun. 19, 2020, and Korean Patent Application No. 10-2020-0147797, filed on Nov. 6, 2020, with the Korean Intellectual Property Office, the disclosures of which are incorporated by reference in their entirety for all purposes as if fully set forth herein.

TECHNICAL FIELD

The present invention relates to a dehydration catalyst, a method for preparing the same, and a method of preparing an alkene using the same. More particularly, the present invention relates to a dehydration catalyst having excellent catalytic activity characterized by high alcohol conversion rate, high selectivity for alkenes, and low selectivity for by-products and having excellent mechanical properties such as crushing strength; a method for preparing the dehydration catalyst; and a method for preparing an alkene using the dehydration catalyst.

BACKGROUND ART

Alumina catalysts in the form of aluminum oxide are used as acid catalysts due to the intrinsic acid sites thereof or as active ingredients such as dispersants for organic/inorganic catalysts due to high stability thereof in the catalyst industry.

In general, in the case of an alumina catalyst, alumina of various phases (e.g., crystal phase) is obtained through a sintering process using aluminum hydroxide or an acid precursor as a precursor. In this case, as burning temperature increases, a stable alumina crystal phase is formed.

Accordingly, when high crushing strength or chemical resistance/corrosion resistance is required in the industry, a stable alumina phase formed through a high-temperature burning process is used.

Compared to an alumina crystal phase obtained by burning at low temperature, an alumina crystal phase obtained by burning at high temperature has high stability, but the alumina crystal phase obtained by burning at high temperature has problems in that the inherent acid sites of alumina and a large specific surface area as a dispersant are remarkably reduced. Thus, the usefulness of the alumina crystal phase obtained by a high-temperature burning process is significantly reduced.

In addition, conventionally, only gamma-phase alumina formed at relatively low temperature exhibits effective activity as a catalyst for isopropyl alcohol dehydration, and theta-phase and alpha-phase alumina formed at relatively high temperature exhibit significantly reduced activity.

Therefore, it is necessary to develop a catalyst having effective activity as a catalyst for isopropyl alcohol dehydration, like a gamma-phase alumina catalyst, and having excellent crushing strength and corrosion resistance/chemical resistance.

DISCLOSURE

Technical Problem

Therefore, the present invention has been made in view of the above problems, and it is one object of the present invention to provide a dehydration catalyst having excellent catalytic activity characterized by high conversion rate for a precursor such as alcohols, in particular, isopropyl alcohol, high selectivity for propylene, and low selectivity for by-products having 3 or more carbon atoms and having excellent mechanical properties such as crushing strength; a method of preparing the dehydration catalyst; and a method of preparing an alkene using the dehydration catalyst.

The above-mentioned object and other objects can be accomplished by the present disclosure described below.

Technical Solution

In accordance with one aspect of the present invention, provided is a dehydration catalyst, wherein the dehydration catalyst is mixed-phase alumina including 1 to 18% by weight of alpha-alumina, 65 to 95% by weight of theta-alumina, and 4 to 34% by weight of delta-alumina.

The dehydration catalyst is preferably a catalyst for alcohol dehydration, more preferably a catalyst for isopropyl alcohol dehydration.

In accordance with another aspect of the present invention, provided is a method for preparing a dehydration catalyst, the method including burning an alumina precursor; performing steam treatment using a gas mixture of water vapor and nitrogen after the burning; and performing, after the performing of steam treatment, burning to obtain mixed-phase alumina including 1 to 18% by weight of alpha-alumina, 65 to 95% by weight of theta-alumina, and 4 to 34% by weight of delta-alumina.

The method for preparing a dehydration catalyst is preferably a method for preparing a catalyst for alcohol dehydration, more preferably a method of preparing a catalyst for isopropyl alcohol dehydration.

In accordance with yet another aspect of the present invention, provided is a method of preparing an alkene, the method including dehydrating an alcohol using the dehydration catalyst of the present invention.

The alcohol and the alkene are preferably isopropyl alcohol and propylene, respectively.

Advantageous Effects

According to the present invention, a dehydration catalyst having excellent catalytic activity characterized by increase in the conversion rate of a precursor such as alcohols, in particular, isopropyl alcohol, high selectivity for a product such as alkenes, in particular, propylene, and low selectivity for by-products and having mechanical properties such as crushing strength; and a method of preparing the dehydration catalyst can be provided.

Specifically, the present invention can provide a catalyst for isopropyl alcohol dehydration having high isopropyl alcohol conversion rate and high selectivity for propylene, thereby improving process efficiency, and having low selectivity for by-products having 3 or more carbon atoms, thereby increasing separation efficiency in a rear-end separation process; and a method of preparing the catalyst.

In addition, the present invention can provide a method of preparing an alkene or propylene having high selectivity for an alkene or propylene and high process efficiency.

DESCRIPTION OF DRAWINGS

FIG. 1 is a graph showing the results of X-ray diffraction (XRD) analysis of a catalyst for isopropyl alcohol dehydration prepared according to Example 1 of the present invention.

FIG. 2 is a graph showing the results of X-ray diffraction (XRD) analysis of a catalyst for isopropyl alcohol dehydration prepared according to Example 2 of the present invention.

FIG. 3 is a graph showing the results of X-ray diffraction (XRD) analysis of a catalyst for isopropyl alcohol dehydration prepared according to Comparative Example 1 of the present invention.

FIG. 4 is a graph showing the results of X-ray diffraction (XRD) analysis of a catalyst for isopropyl alcohol dehydration prepared according to Comparative Example 2 of the present invention.

DETAILED DESCRIPTION

Hereinafter, a dehydration catalyst, a method for preparing the same, and a method for preparing an alkene using the same according to the present invention will be described in detail.

The present inventors confirmed that, when the weights of various crystalline alumina were adjusted to a specific range and the alumina was used to dehydrate isopropyl alcohol, isopropyl alcohol conversion rate and selectivity for propylene were increased and selectivity for by-products was reduced, thereby improving catalytic activity and crushing strength. Based on these results, the present inventors conducted further studies to complete the present invention.

The dehydration catalyst of the present invention is mixed-phase alumina including 1 to 18% by weight of alpha-alumina, 65 to 95% by weight of theta-alumina, and 4 to % by weight of delta-alumina. In this case, its stability can be excellent due to high crushing strength, and its catalytic activity can be improved.

The dehydration catalyst is preferably a catalyst for alcohol dehydration, more preferably a catalyst for isopropyl alcohol dehydration.

The mixed-phase alumina preferably includes 3 to 15% by weight of alpha-alumina, 70 to 85% by weight of theta-alumina, and 10 to 27% by weight of delta-alumina. In this case, stability and mechanical properties such as crushing strength can be improved.

For example, in the mixed-phase alumina, based on 100% by weight of the mixed-phase alumina, alpha-alumina can be included in an amount of 3 to 15% by weight, preferably 5 to 15% by weight, more preferably 5 to 10% by weight. Within this range, catalytic activity can be improved.

For example, in the mixed-phase alumina, based on 100% by weight of the mixed-phase alumina, theta-alumina can be included in an amount of 70 to 85% by weight, preferably 70 to 80% by weight, more preferably 70 to 75% by weight. Within this range, since the catalyst can have excellent mechanical strength, the catalyst can be prevented from being broken during regeneration or catalyst circulation.

For example, in the mixed-phase alumina, based on 100% by weight of the mixed-phase alumina, delta-alumina can be included in an amount of 10 to 27% by weight, preferably 10 to 25% by weight, more preferably 20 to 25% by weight. Within this range, mechanical strength such as crushing strength can be excellent, thereby increasing resistance to external impact.

For example, the mixed-phase alumina may not include gamma-alumina. In this case, high crushing strength and excellent catalytic activity, which are the desired effects of the present invention, can be simultaneously implemented.

In this specification, the absence of gamma-alumina means that the content of gamma-alumina is less than 0.5% by weight, preferably 0.1% by weight or less, more preferably 0.01% by weight or less. Specifically, the absence of gamma-alumina means that no gamma-alumina is detected by XRD analysis according to this specification.

In addition, the mixed-phase alumina can include 1 to 18% by weight of alpha-alumina, 65 to 95% by weight of theta-alumina, 4 to 34% by weight of delta-alumina, and 0% by weight of gamma-alumina. In this case, the activity and strength of a catalyst, which were known to have an inverse relationship, can be simultaneously excellent.

In this specification, when the weights of alpha-alumina, theta-alumina, delta-alumina, and gamma-alumina are measured, an XRD graph is obtained at 10 to 80° (step: 0.05°, measurement time per step: 1 s) using an X-ray diffraction analyzer (Bruker Co.) having Cu radiation (30 kV, 10 mA). Then, based on the XRD analysis data, a structure is analyzed through Rietveld refinement to calculate content ratio (% by weight).

Since the catalyst of the present invention is mixed-phase alumina containing an excess of theta-phase alumina, the catalyst has excellent mechanical strength such as crushing strength and excellent catalytic activity. In particular, the catalyst has an advantage of being able to work at high temperatures.

For reference, in the order of gamma-alumina, delta-alumina, theta-alumina, and alpha-alumina, the catalytic activity decreases, but the strength of the catalyst increases. That is, it was known that the activity and strength of the catalyst are inversely proportional. However, unexpectedly, the alumina catalyst of the present invention has an advantage of simultaneously having high strength of theta-alumina and high activity of gamma-alumina.

For example, the catalyst can have a precursor or alcohol conversion rate of 95% or more, preferably 95 to 100%, more preferably 98.5 to 99.9%, still more preferably 99.4 to 99.9%. Within this range, process efficiency can be improved.

As a specific example, the catalyst can have an isopropyl alcohol (IPA) conversion rate of 95% or more, preferably 95 to 100%, more preferably 98.5 to 99.9% still more preferably 99.4 to 99.9%. Within this range, process efficiency can be improved.

For example, the catalyst can have a product or alkene selectivity of 95% or more, preferably 98.8 to 100%, more preferably 99.1 to 99.9% Within this range, process efficiency can be improved.

As a specific example, the catalyst can have a propylene selectivity of 95% or more, preferably 98.8 to 100%, more preferably 99.1 to 99.9%. Within this range, process efficiency can be improved.

For example, the catalyst can have a by-product selectivity of 5% or less, preferably more than 0% and less than or equal to 3%, more preferably 0.1 to 1% as calculated by Equation 3 below. Within this range, the efficiency of a rear-end separation process can be improved.

By-product selectivity=[(Number of moles of by-products)/(Number of moles of precursor or alcohol reacted)]×100    [Equation 3]

The by-product selectivity preferably refers to selectivity for by-products having 3 or more carbon atoms. In this case, the by-products having 3 or more carbon atoms can be compounds having 3 or more carbon atoms, e.g., diisopropyl ether (DIPE).

In addition, for example, the conversion rate, selectivity, and by-product selectivity can be obtained by analyzing the contents of components in a composition (product) using gas chromatography.

For example, the catalyst can have a crushing strength of 63 N or more, preferably 70 N or more, more preferably 70 to 100 N. Within this range, mechanical properties can be excellent.

In this specification, to measure crushing strength, a single particle was pressed at a constant speed of 0.01 mm/s using a texture analyzer (model: TA-XT2 Plus, Stable Micro System Co.). At this time, the maximum force that the single particle could withstand was measured as crushing strength. For each sample, 2 to 10 particles were measured and the average value thereof was used.

For example, the catalyst can have a specific surface area of 30 m$^2$/g or more, preferably 35 m$^2$/g or more, more preferably 35 to 85 m$^2$/g. Within this range, the activity, strength, and stability of the catalyst can be excellent.

In this specification, for example, the specific surface area can be obtained by measuring the adsorption/desorption amount of nitrogen according to partial pressure (0.10<p/p$_0$<0.25) using a BELSORP-mini II (Mictrotrac-BEL Co.).

For example, the catalyst can have a pore volume of 0.60 cm$^3$/g or less, preferably 0.45 to 0.55 cm$^3$/g. Within this range, the activity, strength, and stability of the catalyst can be excellent.

In this specification, for example, the pore volume can be calculated using an adsorption amount at a partial pressure (p/p$_0$) of 0.99 using a BELSORP-mini II (Mictrotrac-BEL Co.).

For example, the alumina catalyst can include a halogen component in an amount of 0.5% by weight or less, or 0.1 to 0.4% by weight. In this case, catalytic activity can be improved.

The halogen component, preferably chlorine, is combined with the aluminum element of an alumina catalyst to weaken the properties of the Lewis acids of the alumina, thereby facilitating desorption of a product and suppressing formation of by-products.

In this specification, halogen components can be measured using an inductively coupled plasma (ICP) method.

Hereinafter, a method of preparing a dehydration catalyst according to the present invention will be described in detail. In the following description of the preparation method, all the contents of the dehydration catalyst described above are included.

For example, the method of preparing a dehydration catalyst according to the present invention can include a step of burning an alumina precursor; a step of performing steam treatment using a gas mixture of water vapor and nitrogen after the step of burning; and a step of performing, after the step of performing steam treatment, burning to obtain mixed-phase alumina including 1 to 18% by weight of alpha-alumina, 65 to 95% by weight of theta-alumina, and 4 to 34% by weight of delta-alumina. In this case, the stability and activity of a catalyst can be improved at the same time, and an alumina catalyst having high mechanical strength and high corrosion resistance/chemical resistance can be prepared.

As another example, the method of preparing a dehydration catalyst can include a step of performing primary burning of an alumina precursor to obtain first alumina; a step of performing steam treatment with water vapor at a temperature lower than the burning temperature after the step of performing primary burning; and a step of performing, after the step of performing steam treatment, secondary burning at a temperature higher than the steam treatment temperature and lower than the primary burning temperature to obtain mixed-phase alumina including 1 to 18% by weight of alpha-alumina, 65 to 95% by weight of theta-alumina, and 4 to 34% by weight of delta-alumina. In this case, the stability and activity of a catalyst can be improved at the same time, and crushing strength can be improved.

The method of preparing a dehydration catalyst is preferably a method of preparing a catalyst for alcohol dehydration, more preferably a method of preparing a catalyst for isopropyl alcohol dehydration.

For example, the step of performing primary burning can be a step of burning an alumina precursor at a primary burning temperature. In this case, a catalyst having high crushing strength can be easily prepared.

Any materials that can be subjected to burning to provide an alumina crystal phase can be used as the alumina precursor without particular limitation. For example, the alumina precursor can include one or more selected from gibbsite, bayerite, boehmite, and diaspore. In this case, the crushing strength of a prepared catalyst can be improved.

For example, the primary burning temperature can be 800 to 1,100° C., preferably 850 to 1,100° C., more preferably 950 to 1,000° C. Within this range, among various crystal phases, mixed-phase alumina containing an excess of theta-phase alumina can be prepared, and the mechanical strength of the catalyst can be improved.

For example, the step of performing primary burning can be performed for 8 to 12 hours, preferably 9 to 11 hours, more preferably 9 to 10 hours. Within this range, structural change due to heat can be prevented, and mechanical strength can be excellent, thereby increasing resistance to external impact.

For example, the step of performing steam treatment can be a step of performing, after the step of performing primary burning, steam treatment with water vapor at a temperature lower than the primary burning temperature for activation.

In this specification, steam treatment refers to supply of water vapor (steam) using nitrogen as a carrier gas into a reactor set to a specific temperature.

For example, the steam treatment can refer to supply of water vapor and nitrogen into a reactor in the presence of the mixed-phase alumina.

For example, the mixing ratio of nitrogen to water vapor (the volume ratio of N$_2$:H$_2$O) is preferably 1,500:1 to 10,000:1, more preferably 2,000:1 to 3,000:1. Within this range, catalytic activity can be improved while maintaining excellent mechanical strength and chemical resistance.

In addition, for example, the mixing ratio (weight ratio) of the first alumina and water vapor is preferably 1:0.01 to 1:100. As another example, based on 75 g of the first alumina, water vapor (H$_2$O) can be fed at a rate of 0.026 to 0.1 g/min. Within this range, high mechanical strength and high corrosion resistance/chemical resistance can be achieved, and thus an alumina catalyst having high stability and activity can be prepared.

For example, the steam treatment temperature can be lower than the primary burning(calcination) temperature. Preferably, the steam treatment temperature is lower than secondary burning(calcination) temperature to be described below.

For example, the steam treatment temperature can be a temperature inside a reactor. As a specific example, the steam treatment temperature can be 200 to 500° C., preferably 300 to 450° C. Within this range, in the secondary burning step to be described later, activation optimized for burning can be achieved.

For example, the activation step can be a step of performing steam treatment for 1 to 10 hours, preferably 3 to 6 hours. Within this range, high crushing strength and high corrosion resistance/chemical resistance can be implemented, and thus an alumina catalyst having high stability and activity can be prepared.

For example, the step of performing secondary burning can be a step of performing burning at a temperature higher than the steam treatment temperature and lower than the primary burning temperature after the activation step.

For example, the secondary burning temperature can be greater than 500° C. and less than or equal to 600° C., preferably greater than 500° C. and less than or equal to 580° C., more preferably 520 to 580° C. Within this range, the catalytic activity and stability of the mixed-phase alumina activated in the steam treatment step can be improved.

For example, the step of performing secondary burning can be performed for 3 to 7 hours, preferably 3 to 6 hours, more preferably 4 to 6 hours. Within this range, an alumina catalyst having high isopropyl alcohol conversion rate, high selectivity for propylene, and low selectivity for by-products having three or more carbon atoms can be prepared.

For example, the method of preparing an alkene according to the present invention can be performed by dehydrating an alcohol in the presence of the above-described catalyst for alcohol dehydration.

As a preferred example, the method of preparing an alkene according to the present invention can be performed by dehydrating isopropyl alcohol in the presence of the above-described catalyst for isopropyl alcohol dehydration. In this case, the method of preparing an alkene can be referred to as a method of preparing propylene.

For example, the dehydration can be performed by passing a precursor such as alcohols through a reactor filled with the alumina catalyst for dehydration of the present invention.

As a preferred example, the dehydration can be performed by passing isopropyl alcohol through a reactor filled with the alumina catalyst for isopropyl alcohol dehydration of the present invention.

As a specific example, the dehydration can include a step of filling a reactor with the catalyst of the present invention; and a step of continuously passing an alcohol, preferably isopropyl alcohol, through the reactor filled with the catalyst to perform dehydration.

Any reactors commonly used in the art to which the present invention pertains can be used as the reactor of the present invention without particular limitation. For example, a metal tube reactor, a multi-tubular reactor, or a plate-type reactor can be used.

For example, based on a total volume inside a reactor, the catalyst can be included in an amount of 10 to 50% by volume or 10 to 25% by volume.

For example, the dehydration can be performed at 200 to 400° C. and 10 to 30 atm. Within this range, reaction efficiency can be excellent without excessive energy consumption, thereby increasing productivity for a product such as propylene.

As a specific example, the dehydration can be performed at 200 to 400° C., preferably 250 to 320° C.

In addition, the dehydration can be performed at 10 to 30 atm, preferably 15 to 25 atm.

Hereinafter, the present invention will be described in more detail in the following preferred examples. However, these examples are provided for illustrative purposes only and should not be construed as limiting the scope and spirit of the present invention. In addition, it will be apparent to those skilled in the art that various changes and modifications can be made without departing from the spirit and scope of the present invention, and such changes and modifications are also within the scope of the appended claims.

EXAMPLES

Example 1

Boehmite was subjected to burning at 950° C. under an air atmosphere for 10 hours to obtain first alumina, a tubular reactor was filled with the first alumina, the temperature of the tubular reactor was set to 400° C., and then steam treatment was performed by supplying water vapor and nitrogen into the reactor for 3 hours. At this time, water vapor was supplied at a rate of 0.026 to 0.1 g/min using an HPLC pump, nitrogen was supplied at a rate of 133 ml/min using a mass flow controller (MFC), the mixing ratio of nitrogen to water vapor (the volume ratio of $N_2:H_2O$) was 2,500:1, and the weight ratio of water vapor to the first alumina was 0.01 to 100:1. In addition, after steam treatment, burning was performed at 550° C. for 5 hours to obtain an alumina catalyst including 5% by weight of alpha-alumina, 70% by weight of theta-alumina, 25% by weight of delta-alumina, and 0% by weight of gamma-alumina.

Example 2

The process was performed in the same manner as in Example 1, except that primary burning of boehmite was performed at 1,100° C. As a result, an alumina catalyst including 10% by weight of alpha-alumina, 70% by weight of theta-alumina, 20% by weight of delta-alumina, and 0% by weight of gamma-alumina was obtained.

Comparative Example 1

Boehmite was subjected to burning at 550° C. under an air atmosphere for 10 hours to obtain 100% gamma-phase alumina.

Comparative Example 2

Boehmite was subjected to burning at 550° C. under an air atmosphere for 10 hours to obtain 100% gamma-phase alumina, a tubular reactor was filled with the gamma-phase alumina, the temperature of the tubular reactor was set to 400° C., and then steam treatment was performed by supplying water vapor and nitrogen into the reactor for 3 hours. At this time, water vapor was supplied at a rate of 0.026 to 0.1 g/min using an HPLC pump, nitrogen was supplied at a rate of 133 ml/min using a mass flow controller (MFC), the mixing ratio of nitrogen to water vapor (the volume ratio of $N_2:H_2O$) was 2,500:1, and the weight ratio of water vapor to the gamma-phase alumina was 0.01 to 100:1. In addition, after steam treatment, burning was performed at 550° C. for 5 hours to obtain an alumina catalyst composed of 100% gamma-phase alumina.

Test Examples

The properties of catalysts prepared according to Examples 1 and 2 and Comparative Examples 1 and 2 were measured according to the following methods, and the results are shown in Tables 1 and 2.

Test Example 1: Evaluation of Catalytic Activity

The catalytic activities of the prepared catalysts were evaluated through reaction of producing propylene by dehydration of isopropyl alcohol (IPA).

Specifically, 0.75 to 1.5 g of the prepared catalyst was placed in a 1 inch fixed-bed reactor, and reaction was performed by passing isopropyl alcohol through the reactor at a rate of 0.01 to 0.1 g/min.

At this time, the conditions of the fixed-bed reactor were set as follows: a pressure of 20 atm; a reaction temperature of 280° C.; and a WHSV of 0.7 $h^{-1}$. After an IPA dehydration test, the contents of the components of a composition (product) were analyzed using a gas chromatograph connected to the reactor. Based on the analysis results, IPA conversion rate (calculated using Equation 1), propylene selectivity (calculated using Equation 2), and by-product selectivity (calculated using Equation 3) were calculated, and the results are shown in Table 1 below. Here, a gas chromatograph (model name: Agilent 7890B GC, column: HP-1 (100 m×250 μm×0.5 μm), Agilent Co.) was used, and analysis conditions were as follows. Carrier gas: helium (flow rate of 1 mL/min), detector: F.I.D, sampling loop volume: 1 mL (split ratio of 50:1), and heating mode: 50° C./10 min→100° C./0 min (temperature rise at 5° C./min)→200° C./0 min (temperature rise at 10° C./min). In this case, 0 min means not staying at the corresponding temperature.

Conversion rate (%)=[(Number of moles of IPA reacted)/(Number of moles of IPA supplied)]× 100    [Equation 1]

Selectivity (%)=[(Number of moles of propylene produced)/(Number of moles of IPA reacted)]× 100    [Equation 2]

By-product selectivity (%)=[(Number of moles of by-products)/(Number of moles of precursor or alcohol reacted)]×100    [Equation 3]

TABLE 1

| Classification | IPA conversion rate (%) | Propylene selectivity (%) | C3 ≤ by-product selectivity (%) |
|---|---|---|---|
| Example 1 | 99.4 | 99.1 | <1.0 |
| Example 2 | 98.5 | 98.8 | <1.0 |
| Comparative Example 1 | 98.2 | 99.0 | <1.0 |
| Comparative Example 2 | 98.0 | 99.0 | <1.0 |

As shown in Table 1, it can be confirmed that the alumina catalysts according to Examples 1 and 2 of the present invention exhibit IPA conversion rate and propylene selectivity equal to or superior to those of the alumina catalysts (Comparative Examples 1 and 2) composed of 100% gamma-phase alumina. In addition, there is no difference in by-product selectivity. In addition, the alumina catalysts according to Examples 1 and 2 of the present invention have excellent IPA conversion rate and propylene selectivity, thereby improving process efficiency.

In addition, the catalysts according to Examples 1 and have low by-product selectivity, thereby increasing separation efficiency in a rear-end separation process. For reference, the rear-end separation process is a process of separating water and by-products generated during dehydration. Specifically, the rear-end separation process is a process of liquefying DIPE, which is a by-product, by lowering the temperature at the rear end of a reactor to separate water and the by-product. Accordingly, as by-products decrease in the rear-end separation process, separation efficiency increases.

Test Example 2: Evaluation of Crushing Strength

To evaluate the crushing strength of the prepared catalysts, a single particle was pressed at a constant speed of 0.01 mm/s using a texture analyzer (model: TA-XT2 Plus, Stable Micro System Co.). At this time, the maximum force that the single particle could withstand was measured as crushing strength. For each sample, 2 to 10 particles were measured and the average value thereof was used. The results are shown in Table 2 below.

TABLE 2

| Classification | Crushing strength (N/particle) |
|---|---|
| Example 1 | 80 or more |
| Example 2 | 83 or more |
| Comparative Example 1 | 45 or more |
| Comparative Example 2 | 45 or more |

As shown in Table 2, it can be confirmed that, compared to the alumina catalysts (Comparative Examples 1 and 2) composed of 100% gamma-phase alumina, the alumina catalysts according to Examples 1 and 2 of the present invention have excellent crushing strength.

In summary, it can be confirmed that the mixed-phase alumina, which is the alumina catalyst of the present invention, has excellent mechanical strength such as crushing strength while having catalytic activity equal to or superior to that of the alumina catalyst composed of 100% gamma-phase alumina. In addition, these results suggest that the alumina catalyst of the present invention can replace a conventional gamma-phase alumina that has been used as a catalyst for isopropyl alcohol dehydration.

The invention claimed is:

1. A dehydration catalyst, wherein the dehydration catalyst is a mixed-phase alumina comprising:
   1 to 18% by weight of alpha-alumina,
   65 to 95% by weight of theta-alumina, and
   4 to 34% by weight of delta-alumina.

2. The dehydration catalyst according to claim 1, wherein the dehydration catalyst is an alcohol dehydration catalyst.

3. The dehydration catalyst according to claim 2, wherein the alcohol is isopropyl alcohol.

4. The dehydration catalyst according to claim 1, wherein the mixed-phase alumina does not comprise gamma-alumina.

5. The dehydration catalyst according to claim 2, wherein the
   dehydration catalyst exhibits an alcohol conversion rate of 95% or more.

6. The dehydration catalyst according to claim 2, wherein the dehydration catalyst exhibits an alkene selectivity of 95% or more.

7. The dehydration catalyst according to claim 1, wherein the dehydration catalyst exhibits a by-product selectivity of 5% or less.

8. The dehydration catalyst according to claim 1, wherein the dehydration catalyst has a crushing strength of 63 N or more.

9. The dehydration catalyst according to claim 1, wherein the dehydration catalyst has a specific surface area of 30 m2/g or more.

10. The dehydration catalyst according to claim 1, wherein the dehydration catalyst has a pore volume of 0.60 cm3/g or less.

11. A method of preparing a dehydration catalyst, the method comprising the steps of:
performing a primary burning of an alumina precursor;
performing a steam treatment using a gas mixture of water vapor and nitrogen after the primary burning; and
performing a secondary burning to obtain a mixed-phase alumina comprising 1 to 18% by weight of alpha-alumina, 65 to 95% by weight of theta-alumina, and 4 to 34% by weight of delta-alumina after the steam treatment.

12. The method according to claim 11, wherein the alumina precursor is one or more selected from the group consisting of gibbsite, bayerite, boehmite, and diaspore.

13. A method of preparing an alkene comprising the step of:
dehydrating an alcohol using the dehydration catalyst according to claim 1.

14. The method according to claim 13, wherein the dehydrating is performed at 200 to 400° C. and 10 to 30 atm.

15. The method of preparing a dehydration catalyst according to claim 11, wherein the steam treatment is performed at a temperature lower than the primary burning temperature, and the secondary burning is performed at a temperature which is higher than the steam treatment temperature and lower than the primary burning temperature.

* * * * *